(12) United States Patent
Andle

(10) Patent No.: US 7,552,619 B2
(45) Date of Patent: Jun. 30, 2009

(54) MEASUREMENT OF DENSITY AND VISCOELASTICITY WITH A SINGLE ACOUSTIC WAVE SENSOR

(75) Inventor: Jeffrey C. Andle, Westbrook, ME (US)

(73) Assignee: Vectron International, Inc., Hudson, NH (US)

( * ) Notice: Subject to any disclaimer, the term of this patent is extended or adjusted under 35 U.S.C. 154(b) by 0 days.

(21) Appl. No.: 10/597,487

(22) PCT Filed: Apr. 22, 2004

(86) PCT No.: PCT/US2004/012546

§ 371 (c)(1),
(2), (4) Date: Feb. 14, 2007

(87) PCT Pub. No.: WO2005/114138

PCT Pub. Date: Dec. 1, 2005

(65) Prior Publication Data

US 2007/0144240 A1    Jun. 28, 2007

(51) Int. Cl.
*G01N 9/02*    (2006.01)

(52) U.S. Cl. .................................... 73/32 A

(58) Field of Classification Search .............. 73/32 R, 73/32 A, 54.24–54.26, 54.32, 54.36, 54.41; 310/313 R, 313 A
See application file for complete search history.

(56) References Cited

U.S. PATENT DOCUMENTS

| | | | |
|---|---|---|---|
| 4,513,261 A | 4/1985 | Yen et al. | 333/194 |
| 4,731,595 A | 3/1988 | Wright | 333/195 |
| 5,708,191 A | 1/1998 | Greenwood et al. | 73/32 A |
| 5,741,961 A | 4/1998 | Martin et al. | 73/32 R |
| 5,798,452 A | 8/1998 | Martin et al. | 73/32 R |
| 5,886,250 A | 3/1999 | Greenwood et al. | 73/32 A |
| 5,932,953 A | 8/1999 | Drees et al. | 310/324 |
| 6,033,852 A | 3/2000 | Andle et al. | 435/6 |
| 6,082,180 A | 7/2000 | Greenwood | 73/32 A |
| 6,082,181 A | 7/2000 | Greenwood | 73/32 A |
| 6,255,915 B1 | 7/2001 | Edmonson | 333/193 |
| 6,543,274 B1 | 4/2003 | Herrmann et al. | 73/32 A |
| 7,007,546 B2 | 3/2006 | Andle | 73/54.41 |

*Primary Examiner*—Hezron Williams
*Assistant Examiner*—Tamiko D Bellamy
(74) *Attorney, Agent, or Firm*—Shalom Wertsberger; Saltamar Innovations

(57) ABSTRACT

A sensor, method and system, for measuring certain characteristics of a fluid. The sensor utilizes a piezoelectric device having at least two tightly coupled resonators providing a two pole electric transfer function responsive to an electrical signal coupled to the input resonator. The piezoelectric sensor has a textured entrapment layer, constructed to entrap a known volume of fluid and impart motion to the entrapped fluid as well as to surrounding non-trapped fluid. The common mode frequency shift of the two resonant frequencies is related to mass loading due to the entrapped fluid, while the energy absorbed by the fluid, or a phase shift of one of the resonant frequencies, is related to the viscosity/density product of the fluid. Extracting the viscosity is a matter of mathematical manipulation. By controlling the energy level of the input electrical signal, the viscosity measurement may be conducted at a predetermined shear rate.

17 Claims, 8 Drawing Sheets

A) FREQUENCY-BASED DENSITY MONITOR

B) FREQUENCY-BASED DENSITY AND POWER-LOSS VISCOSITY MONITOR

C) FREQUENCY-BASED DENSITY AND VISCOSITY MONITOR

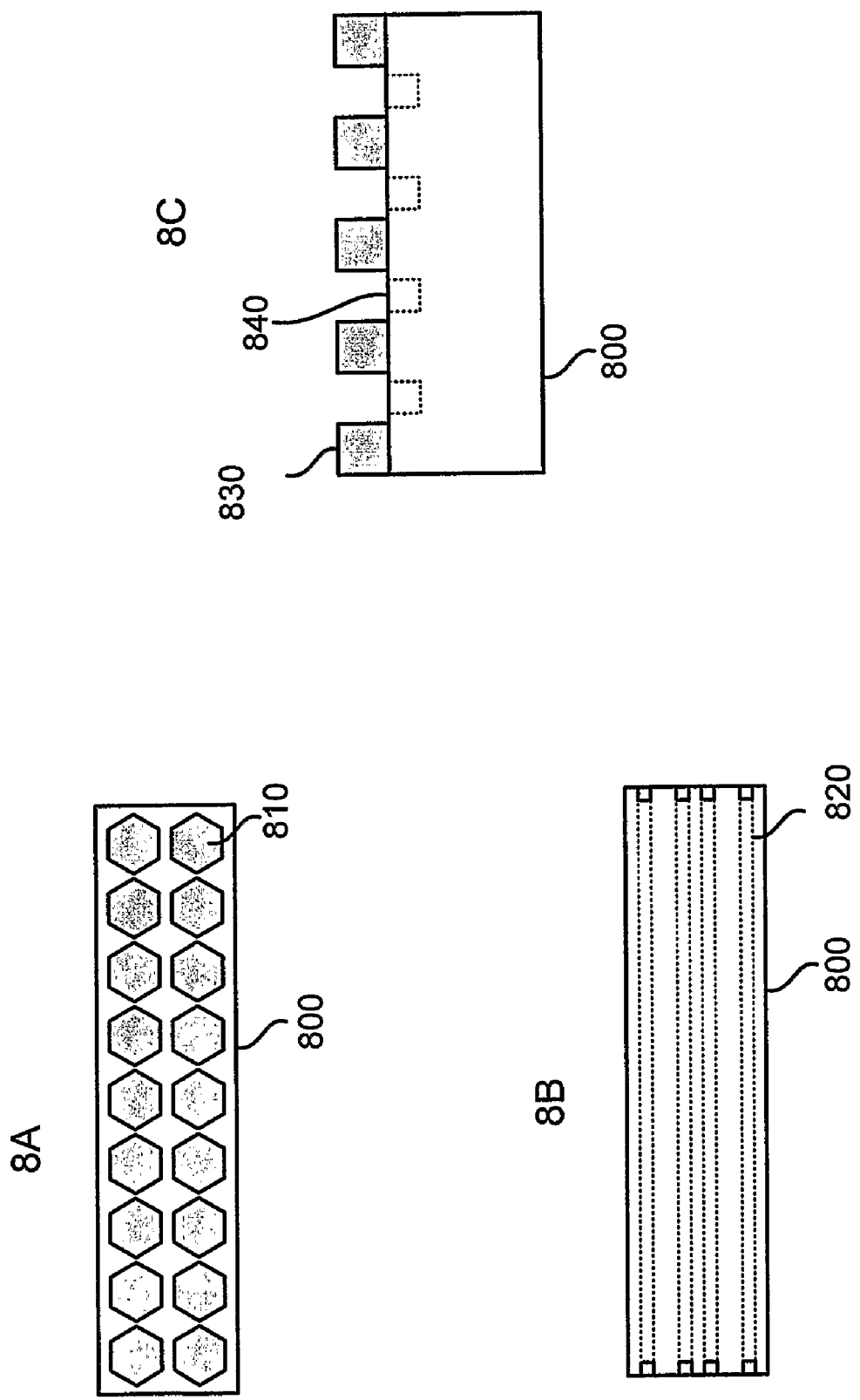

MEASUREMENT OF DENSITY AND VISCOELASTICITY WITH A SINGLE ACOUSTIC WAVE SENSOR

FIELD OF THE INVENTION

This application is directed generally to the real-time measurement of liquid density using acoustic wave sensors; and more particularly to methods of distinguishing density information from viscosity information using a single sensor.

BACKGROUND OF THE INVENTION

Density, also referred to as specific gravity, is an important process variable in liquid phase manufacturing processes. Density is defined as the mass of a material divided by its volume. To date, no good method of continuously monitoring the property exists. Solid state measurements of density that are suitable for in-process measurements either require multiple sensors or prior knowledge of additional material parameters (e.g. compressional elastic modulus or viscosity) or carefully controlled flow properties (e.g. in a coriolis force measurement.

Viscosity and, more generally, viscoelasticity, are properties of liquids and solids that relate the shear forces generated by or applied to a material to the amount of shear deformation or flow. While the present invention applies equally well to viscoelasticity, for the sake of clarity and simplicity, this disclosure will use viscosity as an example, with the understanding the invention extends to other viscoelastic characteristics. Viscosity is of widespread interest in many manufacturing environments and is measured as a primary quality of some products and as a secondary quality (a means of monitoring process state) in other processes. In many of these applications, measurement of density is also a requirement.

Viscosity describes the force required in order to make successive molecular layers of a liquid move past each other at a given rate of shear ("shear rate"). If one considers a liquid flowing past the walls of a container, the liquid will typically have no motion relative to the wall at the interface and will have increasingly higher velocities as one observes points successively further from the wall. The shear rate is defined as the gradient of the velocity of the liquid parallel to the surface (meters per second) with increasing distance from the surface (meters). The units of shear rate are 1/seconds. The shear stress is the amount of force per unit area that must be applied in order to cause the motion.

Hydrodynamic properties of liquids are quantified by the speed of shear sound waves in a liquid. An ideal liquid, having neither shear elasticity nor viscosity, cannot support a shear sound wave. An elastic solid having a shear stiffness, $\mu_s$, can support a shear acoustic wave that propagates through the solid much as the better known compressional sound wave. The velocity of the wave is $(\mu_s/\rho_s)^{1/2}$, where $\rho_s$ is the solid's density. Viscous liquids can support a shear sound wave; however the wave decays as it travels and is only able to travel a few wavelengths before being totally dampened out by frictional losses. The complex velocity of these waves is $(j\omega\eta/\rho)^{1/2}=(1+j)(\omega\eta/2\rho)^{1/2}$. Measurement of the shear wave velocity thus provides information on the ratio of liquid's viscosity to its density and can thus be used to measure density if viscosity data is available.

These "sound waves" are related to the flow of liquids in confined geometries, such as capillaries, pipes and the spaces between moving parts in machinery. These flows are governed by the ratio of the intrinsic viscosity, $\eta$, to the density of the material, $\rho$. The ratio is known as the "kinematic viscosity", $\eta_k=\eta/\rho$, and has the units of area over time (m²/s).

There exist densitometers which measure changes in the resonant frequency of a tuning fork as it is filled with the test liquid. The method is highly susceptible to vibration. It is an object of the present invention to provide a sensor that is immune to most vibration levels. One method of reducing susceptibility to vibration while employing the resonant measurement method is to employ a high frequency (MHz) resonator, such that the vibrations are well outside the frequency band of the instrument.

Compressional acoustic wave devices measure the product of elastic modulus and density (acoustic impedance) or the ratio therebetween (acoustic velocity) and offer one potential avenue of obtaining both values from a single "measurement". However, the complexity of the structure and of the signal analysis has severely limited this approach for transmission based systems (acoustic spectroscopy). Typically these systems employ pulse echo systems in which a signal undergoes multiple transmissions through the test sample. The systems are extremely dependent on accurate knowledge of the path length in the sample. A preferred solution would employ a single point of contact and localized measurement.

Tuning fork methods measure the product of density and elastic modulus or the product of density and viscosity and are presently sold as densitometers. They attribute downward shifts of the resonant frequency to density (ignoring elastic modulus) and decreases in resonant quality factor (increased damping) to the viscosity-density product. The methods require prior knowledge of the elastic modulus and careful control of the depth of insertion of the tuning fork into the sample. A method is desired in which the depth of insertion is not critical and in which no other parameter need be known other than those measured by the sensor itself, or a small number of other sensors that may be coupled within a limited area or enclosure, to provide data on localized conditions.

In addition to the propagation of acoustic waves through a material, it is possible to employ acoustic waves in an adjacent solid to measure the power transfer into the viscous liquid. Power transfer from one medium to the other is governed by the ratio of the acoustic impedances of the materials. Power transfer of acoustic energy between a solid waveguide and an adjacent liquid forms the basis of several viscometers. The rate of energy transfer (power loss) is dependent on the relative acoustic impedances of the waveguide material and the adjacent liquid in a manner well-known to one skilled in the art. The acoustic impedance of the shear wave in the solid waveguide is the square root of the product of the density, $\rho_s$, and the shear elastic stiffness, $\mu_s$. It is predominantly real (resistive) and is analogous to a nearly-lossless transmission line's characteristic impedance in electromagnetics. The acoustic impedance of a shear wave in a viscous liquid is the square root of the product of the stiffness term, $j\omega\eta$, with the density, $\rho$. The characteristic impedance of the viscous liquid is typically very small compared to the elastic solid, resulting in a low power transfer. At low viscosity the power transfer is proportional to $(\omega\rho\eta)^{1/2}$. Therefore, if the viscosity is known, density can be measured.

U.S. Pat. No. 5,708,191 Greenwood et al., U.S. Pat. No. 5,886,250 Greenwood et al., U.S. Pat. Nos. 6,082,180 and 6,082,181 to Greenwood, present a family of densitometer sensor designs that employ input and output transducers to measure changes in reflected signal strength of acoustic waves as they reflect near a critical angle of incidence. These viscometers measure either viscosity-density product or elasticity-density product based on the reflection of acoustic waves from the liquid-loaded face of a solid material supporting the transducers. The sensors measure reflection coefficients of the wave from solid-liquid boundaries upon a few reflection events of a pulsed or continuous-wave signal. Such methods offer less sensitivity and resolution of the measured quantity than do resonant and multi-reflective devices. The latter enjoy higher sensitivity from the continuous interaction of their acoustic waves with the solid-liquid interface. The discrete-reflection methods do not enjoy the simplicity of manufacture or operation of a continuous acoustic wave interaction surface, nor do they provide similar sensitivity or resolution. Finally, the discrete reflection methods assume a fixed elastic modulus (for the more common compressional wave version) or viscosity (for the less common shear wave version) in order to extract density information from the measured response of the sensor.

Another method of performing the density-viscosity product measurement is to immerse a resonator manufactured on a piezoelectric substrate and supporting a transverse shear mode of resonance, typically a disc of quartz crystal of AT cut, into the liquid and to measure the shift in resonant frequency or the loss of power at resonance. This method has been plagued by poor reproducibility when used with affordable instrumentation, primarily due to the lack of a differential measurement within the sensor.

This issue has been overcome through the use of two-port devices based on multi-pole resonators using shear wave acoustic modes, such as the SH-SAW (Shear Horizontal-Surface Acoustical Wave), SHAPM (Shear Horizontal Acoustical Plate Mode), MPS (Monolithic Piezoelectric Sensor) e.g. as described in U.S. Pat. No. 6,033,852, issued Mar. 7, 2000 to Andle et al.

U.S. Pat. Nos. 5,741,961 and 5,798,452 to Martin et al. disclosed a method in which two acoustic wave sensors having different surface treatment exhibit essentially identical responses to viscosity-density product but differing responses to the density. A reference sensor provides data on the product of viscosity and density and employs a smooth surface. The second sensor has an intentionally roughened surface, typically having grooves or pits in its surface for trapping a certain volume of fluid. The added mass creates a finite frequency shift with little or no power loss in addition to the power loss and frequency shift of the viscously entrained liquid. The difference in the frequency shifts between the two sensors is therefore attributed to the mass of the material trapped in grooves or wells of a textured surface, providing a measure proportional to the density via the frequency difference. The density-viscosity product is available via the common-mode frequency shift. While this method is attractive, it incurs difficulties in sensor-to-sensor reproducibility when the two sensors are manufactured on different substrates.

The addition of such grooves to one of a pair of shear horizontal surface acoustic wave (SH-SAW, also known as Love Wave, surface transverse wave, and the like.) sensors is also disclosed (Herrmann et al., U.S. Pat. No. 6,543,274), and the extension of this approach to SHAPM sensors is contemplated herein. This method offers higher frequency, smaller size, and improved sensitivity at the expense of manufacturing complexity and available dynamic range. However Herrmann still finds the use of two completely identical sensor elements necessary for measuring both parameters, and therefore it does not overcome the sensor-to-sensor limitations of the Martin device.

In a U.S. Pat. No. 7,007,546 to Andle titled "Measurement, Compensation and Control of Equivalent Shear Rate in Acoustic Wave Sensors" (which is incorporated herein by reference in its entirety), the inventor of the present application disclosed a method for measuring viscosity and shear rate at which the measurement is performed by utilizing an acoustic wave sensor, and calculating the shear rate as a function of the characteristic rate of fluid movement in response to a given power transmitted to a fluid, and the viscosity of the fluid. The acoustic wave device has a characteristic relationship between input power, output power, and an acoustic wave amplitude at a selected region between the input and output transducer. The acoustic wave device is coupled to the measured fluid. A predetermined power level $P_{in}$ of a harmonic signal is applied to an input transducer, to impart an acoustic wave at the selected region. Output power level $P_{out}$ is measured at the output transducer. Using the characteristic relationship, and the input and output power levels, the amplitude of the average acoustic wave imparted to the fluid is calculated. Measuring the viscosity of the fluid to obtain a measured viscosity at the selected region, allows calculating of the shear rate of the fluid at the selected region, by using the frequency, the viscosity measurement, and the acoustic wave amplitude. This invention may be beneficially used with the present invention as explained below.

There is therefore a clear and unanswered need for a densitometer, and also for a combination densitometer/viscosity meter, that is reliable, precise, easy to manufacture, and easy to install in various applications, which does not rely necessarily on the use of a plurality of sensors and that is compensated for wide variations in the viscosity of the sample. The preferred embodiments of the present invention provide such solutions.

SUMMARY

It is an object of the present invention to replace the separate textured sensor and smooth reference one port (impedance element) devices with a single two-port (transmission) device while continuing to provide the ability to measure density and viscosity with the device. It is an optional object of the present invention to accomplish the measurement of density in a viscous liquid in a manner that is compatible with previously disclosed measurement and control of the shear rate at which the liquid's viscosity is measured. Other objects of the invention will be clear to the skilled in the art from the description, claims, and drawings of the present application.

The preferred embodiment of the present invention utilizes a device, namely a two-port, two-pole coupled resonator with a textured entrapment layer in contact with a fluid to be measured, such as a liquid or a gas. It further discloses preferred electronic circuits including said device, that enable the user to employ one or more disclosed methods of estimating the density of a viscous liquid, independently or simultaneous with the measurement of viscosity. The preferred embodiment further provides the capacity to measure, and/or control, the shear rate at which the viscosity measurement is conducted.

Optionally, the present invention further allows measuring and controlling the shear rate at which the viscosity is measured, in combination with measuring the density. This offers the distinct advantage of allowing the error due to shear rate dependence of viscosity to be averaged out of the density measurement for complete viscosity compensation of the measured density. It further allows a single sensor to provide data on acoustic viscosity ($\rho\eta$), intrinsic viscosity ($\eta$) and/or kinematic viscosity ($\eta/\rho$) as a function of shear rate, implementing a compact, solid state rheometer for materials characterization and evaluation.

Therefore in an aspect of the present invention there is provided a method for measuring fluid density comprising the steps of providing a sensor, feeding an input electrical signal to the sensor input resonator, and measuring the density of the fluid. The sensor comprises a liquid phase acoustic wave device (LPAWD) having an entrapment layer coupled thereto. The entrapment layer has a textured surface in contact with the fluid, and having a known volume available for entrapping said fluid; the LPAWD has an input and an output transducers electromechanically coupled respectively to a first and second resonators. The resonators being sufficiently coupled therebetween to provide the LPAWD with an electrical transfer function characterized by at least a first resonant frequency $F_S$ and a second resonant frequency $F_A$ at or about 180 phase shift relative to said $F_s$. Preferably, the step of measuring the density further comprises the steps of measuring the second resonant frequency $F_A$; and using the measured resonant frequency, and characteristic response of said LPAWD, to calculate the density of the fluid. The step of measuring further comprises the step of using a calibration function to account for an approximated viscosity of said fluid. Further preferably, the method comprises the steps of providing an amplifier coupled between said input and output transducers, the amplifier having a gain sufficiently high to cause signals therethrough to oscillate at or about $F_A$; and providing a frequency sensing circuit to sense changes in the frequency of oscillations.

In another aspect of the invention, there is provided a method of measuring density and viscosity of a fluid. The method comprising the steps of:

Providing a sensor comprising a liquid phase acoustic wave device (LPAWD) having an entrapment layer coupled thereto or embedded therein, the entrapment layer having a textured surface for contact with the fluid, and having a known volume available for entrapping said fluid. The LPAWD comprises an input and an output transducers electromechanically coupled to a first and second resonators respectively. The resonators are sufficiently coupled therebetween to provide the LPAWD with an electrical transfer function characterized by a first resonant frequency $F_S$, and a second resonant frequency $F_A$ at or about 180 phase shift relative to said $F_s$. An input electrical signal is fed to the input transducer, and the density and viscosity of the fluid are measured. The method preferably comprises the steps of measuring the power difference between the input and output transducers, to obtain a product of the viscosity and density of said fluid, which can then be used in the step of measuring the viscosity. Preferably the step of measuring the density comprises measuring the frequency, $F_A$. The measured density can be used to compensate for density effects on the viscosity measurements, and the measured viscosity can be used to compensate for viscosity effects in measuring the density.

Optionally, the input electrical signal is controlled to produce a predetermined shear rate under which said viscosity is being measured. Further optionally, the shear rate is controlled by controlling the input electrical signal at an energy level, $P_{IN}$, to produce a desired displacement of said entrapment layer.

The energy level, $P_{IN}$, is calculated using the formulae: $\dot{\gamma} = \omega U / \delta$, where $\omega = 2\pi F_A$, $$\delta = \sqrt{\frac{2\eta}{\omega \rho}}$$

is the penetration depth of the wave into a fluid having viscosity, $\eta$, and density, $\rho$, and the acoustic wave amplitude $U = C\sqrt{P_{avg}}$ is determined by a device constant, C, and an energy level, $P_{avg}$, being a geometric mean of power levels measured at said input $P_{IN}$ and output transducers.

In the preferred embodiment of the invention, the step of measuring the density comprises measuring the said second resonant frequency, and the step of measuring the viscosity comprises measuring power insertion loss between said input resonator and output resonator. However in another embodiment, the step of measuring the viscosity comprises measuring the shift of one or both of said resonant frequencies. The preferred embodiment also comprises the step of controlling the energy level of the input electrical signal so as to control the shear rate in which the viscosity is measured.

In another aspect of the invention there is provided a sensor for measuring viscosity and/or density of a fluid, the sensor comprises a substrate having an input and an output transducer, coupled respectively to a first and a second resonator. The resonators are sufficiently closely coupled therebetween, to form a device with an electrical transfer function characterized by at least a first resonant frequency $F_S$, and a second resonant frequency $F_A$ at or about 180 phase shift relative to said frequency $F_s$. The sensor has an entrapment layer coupled to the substrate, or embedded therein. The entrapment layer is coupled to said substrate directly or by an intermediate layer. Preferably, the entrapment layer comprises at least one face having a groove or grooves formed therein (i.e. the grooves may be in the entrapment layer or deposited on it.), for trapping a known volume of the fluid. The grooves are preferably oriented perpendicular to the direction of wave motion in said substrate, and preferably dimensioned to be smaller than the length of a quarter of the wavelengths in the liquid, of said resonant frequency $F_S$. Such grooves may be formed by depositing material on said face to form ridges, the grooves being defined between said ridges. Alternatively, the grooves may be cut (e.g. by drilling, etching, and the like) into the substrate. As one of many alternatives to the grooves, the entrapment layer may comprise at least one chamber formed therein, the chamber having at least one opening for entrapping a known volume of said fluid. The chamber may be cut into the entrapment layer or formed by material deposited thereupon. Most preferably, the entrapment layer is integral to at least one face of the substrate. Also preferably, the entrapment layer covers an approximately equal area of each of said resonators, and at least 50% of the frontal area of each resonator. Most preferably, the textured area covers the whole surface area of at least one face of the entrapment layer. Such a sensor may be used for density measurements alone by measuring the resonant frequency $F_A$.

In yet another aspect of the invention there is provided an apparatus for measuring density and viscosity of a fluid, the apparatus comprising a sensor comprising a substrate having an input and an output transducers coupled respectively to a first and a second resonators; said first and second resonators being sufficiently closely coupled therebetween to form an electrical transfer function characterized by at least a first resonant frequency $F_S$, and a second resonant frequency $F_A$, at or about 180 degrees phase shift to said frequency $F_S$, and an entrapment layer coupled to said substrate, or embedded therein. The system further comprises a first measuring means for measuring the density of said fluid, and a second measuring means for measuring a product of said viscosity and density. Such sensor may be used for density measurements alone by measuring the resonant frequency $F_A$, in which case the second measuring means is not required. The apparatus preferably further comprises a computer adapted for computing the density from the measured product and the measured density. Such computer may be a special purpose computer, or a general purpose computer. Software in the computer may be easily adapted to perform the needed steps. The first measuring means preferably comprises frequency measurement equipment. By way of a non limiting example, the first measuring means can comprise a first oscillator coupled between the input and resonator, constructed to oscillate at 180° phase relative to an input electrical energy inputted to said input transducer, and preferably also a second oscillator coupled between said output and input resonator and constructed to oscillate at or about 0° phase from said input electrical energy. Preferably, the second measuring means comprises circuitry to measure insertion power loss between said input and output transducers. Alternatively, the second measuring means comprises circuitry to measure difference frequencies between said first and second oscillators.

In the most preferable embodiment, the apparatus controls the input energy in order to measure the viscosity at varying shear rate. Optionally, a temperature sensor is further included in the apparatus.

BRIEF DESCRIPTION OF THE DRAWINGS

The invention will be better understood in light of the attached drawings, in which:

FIG. 8a is a front view of an entrapment layer having hexagonal chambers, FIG. 8b is a front view of an entrapment layer having covered tunnels (shown in dashed lines), and FIG. 8c is a side elevation of the entrapment layer, showing two possible methods of construction, i.e. by depositing material on the face, or by removing material from the face. Clearly a combination of those methods is equally applicable.

DETAILED DESCRIPTION

Figure 1:
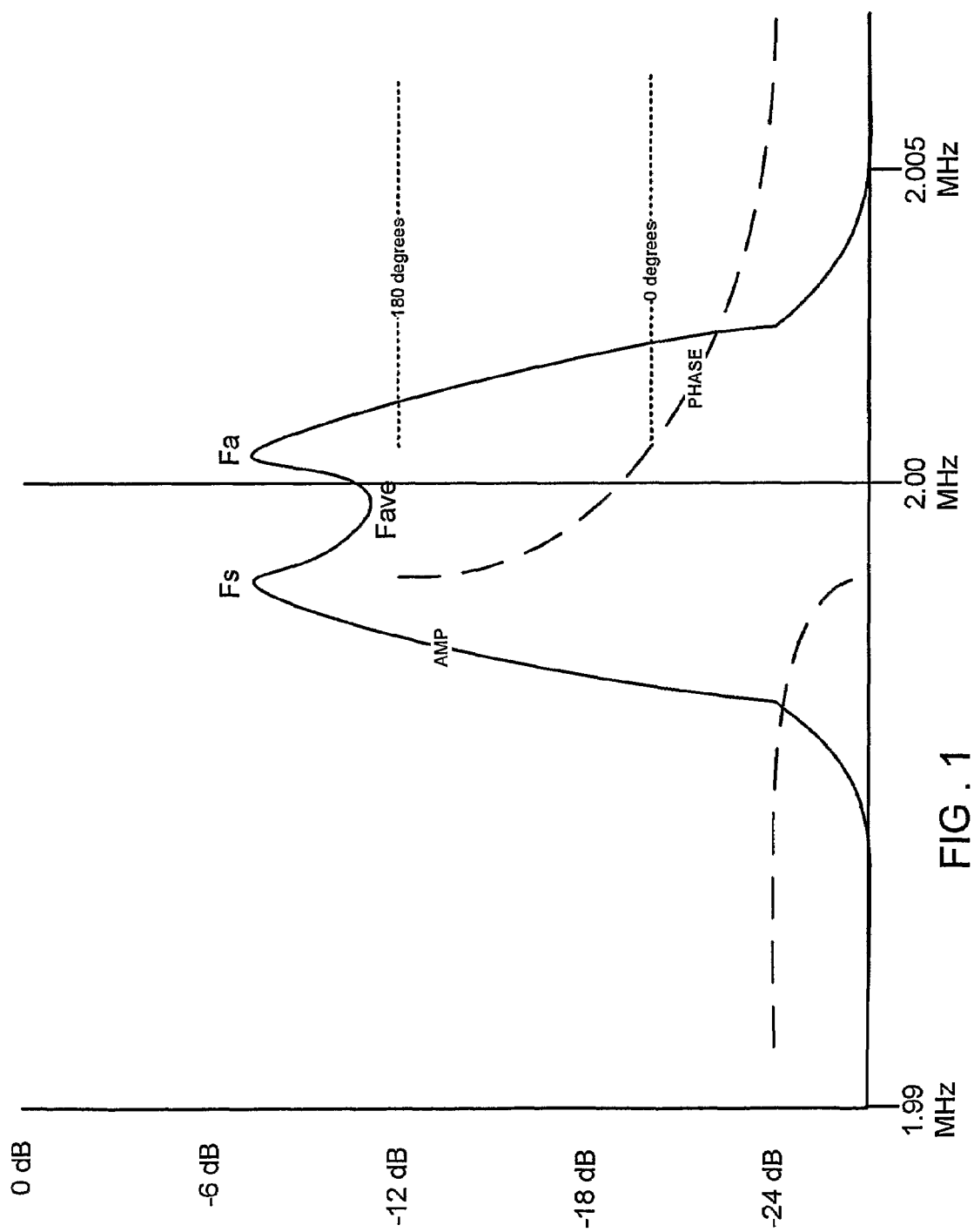
FIG. 1 depicts an example graph of a typical frequency response of a simple two port, two pole acoustic device without any mass-loading or damping effects.

It is an important object of the present invention to provide a method of obtaining the measurements of density and of density-viscosity product, in a single sensor with essentially simultaneous measurement. The aspects of the invention are equally applicable to any shear horizontal (SH) acoustic wave device used to implement the sensor, whether it employs the bulk acoustic wave (BAW) parallel plate resonator, SH acoustic plate mode (SHAPM) parallel plate waveguide, or the SH surface acoustic wave (SH-SAW) planar device structure (commonly known as a Love wave device).

The invention is equally applicable to any acoustic wave device not having SH wave displacements but still having acoustic wave amplitudes confined primarily to the surface plane of the acoustic wave device prior to texturing. It is further applicable to flexural plate wave (FPW) devices employing the slow mode of a thin membrane using either piezoelectric, magnetic, or any other convenient method of acoustic wave transduction. In general, the present invention may be practiced on any acoustic wave device having a combination of wave displacement polarizations and or wave velocity such as to control energy loss caused by contact with a liquid and viscous coupling of energy into said liquid. Generically such a sensor shall be referred to as a liquid phase acoustic wave device (LPAWD). The invention relates to the use of a multi-pole, coupled-resonator filter structure using said LPAWD, with the preferred embodiment having two poles.

An important aspect of the invention is based on a liquid phase acoustic wave device having a substrate and at least two transducers that provide electrical input and output ports. The two transducers are sufficiently tightly coupled to a first and a second resonant structure, said resonant structures coupled to each other, either directly or via additional resonant or transmission structures, so as to exhibit electrical transfer function similar to a resonator filter having at least a dual pole transfer function between the input and the output. The principles of such Two Pole Coupled Resonator Filter structure are explained in more detail in an article by M. G. Schweyer, J. A. Hilton, J. E. Munson, J. C. Andle, J. M. Hammond, and R. M. Lec, titled "A Novel Monolithic Piezoelectric Sensor", published in the 1997 IEEE International Frequency Control Symposium, pp. 32-40 or in an article by M. B. King, L. W. Heep and J. C. Andle, titled "1500 MHz Coupled Resonator Filter", and published in the Proceedings of the 1987 IEEE Ultrasonics Symposium, pp. 127-130.

Such two-pole resonators may be modeled and/or designed based on a structure consisting of two simple resonator structures, one coupled to an input transducer connected between the input connection and ground and the other coupled to an output transducer connected between the output connection and ground, with a coupling mechanism between said resonators. In the preferred embodiment of the present invention, the resonators are acoustic structures of either mirrored plate or grating reflector types, and the coupling to the electrical input and output is accomplished via an appropriate piezoelectric or similar transducer structure. Clearly, other methods of creating such multi-pole-multi-port structures exist, and similarly connection methods may vary as known, e.g. by providing separate floating input and output circuits without a common 'ground'. Magnetostrictive, electrostrictive, piezoresistive and other transduction means are equally viable and shall be inclusively considered as coupling a resonator to an electrical terminal or terminals.

The structure functions by providing a transfer of energy between one resonator and the other due to the coupling mechanism. The result of the coupling is to create a combined device in which there are at least two resonant modes, each being a superposition of the wave envelope supported by the individual resonators. One such combined resonance $F_S$, having the lower frequency and typically 180° of phase shift, has a symmetric superposition, while the other combined resonance $F_A$, having the higher frequency and typically 0° of phase shift, has an antisymmetric superposition. It is not necessary that the two coupled resonators be identical. It is important to note that in order to achieve a two-pole coupled resonator it is insufficient to merely place two independent resonators on a single substrate, but sufficiently close coupling between the resonators is required, to provide the wave interaction described above. The degree of coupling, M, is such that $M=\Delta F/F_0=2(F_A-F_S)/(F_A+F_S)$, results in a quantifiable difference between $F_A$ and $F_S$. One skilled in the art will recognize that the absolute phase shifts of the signal at the two resonances can be altered from the typical values by internal and external influences, including by way of non-limiting example, altering the connection polarity, variations in transducer capacitance, and the use of external phase shifting circuitry. Where the values 180° and 0° are used throughout this document, it should be taken to mean either the actual phase of the signal transmission at $F_S$ or $F_A$ or the phase shift required of an amplifier to oscillate at $F_S$ or $F_A$, as appropriate from the context, and not the specific numerical value, 180° or 0°.

The general shape of such a two-pole frequency transfer function is represented schematically in FIG. 1 in an exaggerated form to increase understanding of the invention. The two pole frequency response graph shows the crystal to have at least two resonant frequencies, i.e. at least one symmetric frequency, $F_S$, and at least one anti-symmetric frequency, $F_A$, having a mutual phase shift therebetween of about 180°. The spread between the resonant frequencies is determined primarily by the level of mutual coupling between the resonator cavities to which the acoustic energy is localized. Highly coupled cavities lead to widely separated resonant frequencies.

Figure 4A:
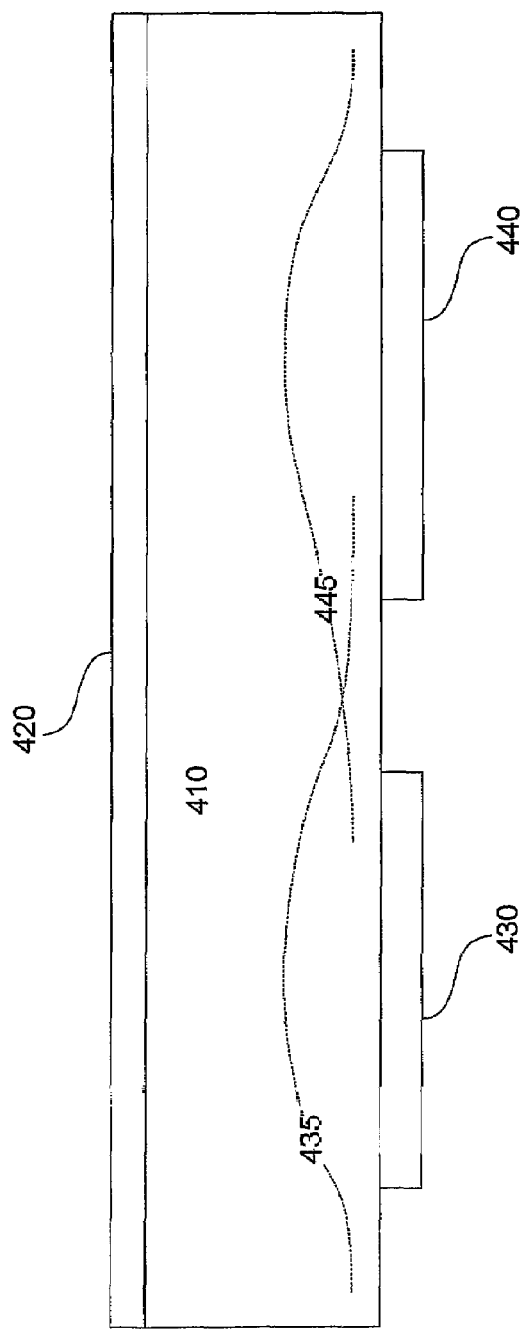
FIGS. 4a and 4b depict elevation and top view of a simplified structure of an acoustic wave device having an entrapment layer according to the preferred embodiment of the invention.

Therefore a preferred embodiment of the invention, depicted schematically in part in FIG. 4a, comprises a piezoelectric substrate 410 having an input transducer 430 and an output transducer 440, each electromechanically coupled to a resonant mechanical structure (depicted schematically as the wave propagation form 435 and 445 respectively) embedded in the substrate. For the purpose of these specifications, The resonant mechanical structure (resonator) is considered 'embedded' in the piezoelectric substrate if it confines acoustic waves within the substrate or at the surface of the substrate, whether or not the whole resonator is contained within the substrate. Alternatively the resonators may be otherwise coupled to said substrate such as being attached to outside surfaces of the substrate but in rigid mechanical coupling thereto, but still be considered 'embedded' into the substrate and practically a portion thereof, as they create the required perturbations therein and the substrate allows for the tight coupling described hereinunder.

The transducers in the preferred embodiments use piezoelectric coupling on a substrate consisting of one or more layers of material, at least one of which is piezoelectric. The most preferable embodiment is an inter-digitated transducer. Alternative embodiments allow for electrical coupling to the mechanical resonators embedded in the substrate using magnetic, electrostrictive, piezoresistive, optical or other equivalent transduction means to convert input electrical signals into mechanical energy trapped within the coupled resonators and to detect said trapped signals and such alternate means of electrically exciting and measuring the acoustic energy in the coupled resonators should be considered within the scope of the present invention.

The input and output resonators, are also coupled to each other via the substrate and are mutually coupled, i.e. the perturbation originating in the input resonator reach the output resonator, and vice versa, so as to provide the desired two pole frequency transfer function. In order to achieve such close coupling the distance between the input and output resonator could be calculated or approximated by methods specific to the particular resonator geometry and widely published in the literature. In general, the calculation involves first estimating the extent of the evanescent or fringing mechanical fields outside one resonator and in the direction of the other resonator, then evaluating the overlap of the fringing fields of one resonator with those of the other resonator, said degree of interaction representing the coupling factor between said resonators. The preferred method of calculation is to treat the structure in cross section as a multi-region, one dimensional waveguide with boundary conditions between said regions of continuity of mechanical amplitude and continuity of mechanical stress. Such boundary value analysis yields coupled differential equations that may be solved for the symmetric and antisymmetric modes of the coupled structure and the associated frequencies. This method of calculating is but one of many known to the skilled in the art, and any convenient method may be used. While the preferred embodiment employs rectangular geometries for manufacturing and analytical simplicity, circular, semicircular, elliptical, hyperbolic, parabolic and other resonator shapes that are equally applicable are known, and in some applications preferred. Similarly, while the preferred embodiment employs polished, parallel surfaces of the piezoelectric substrate, there are in the literature both spherically and aspherically contoured resonator structures that are preferable in select applications to better trap the acoustic energy albeit at the cost of increased manufacturing complexity.

Figure 2:
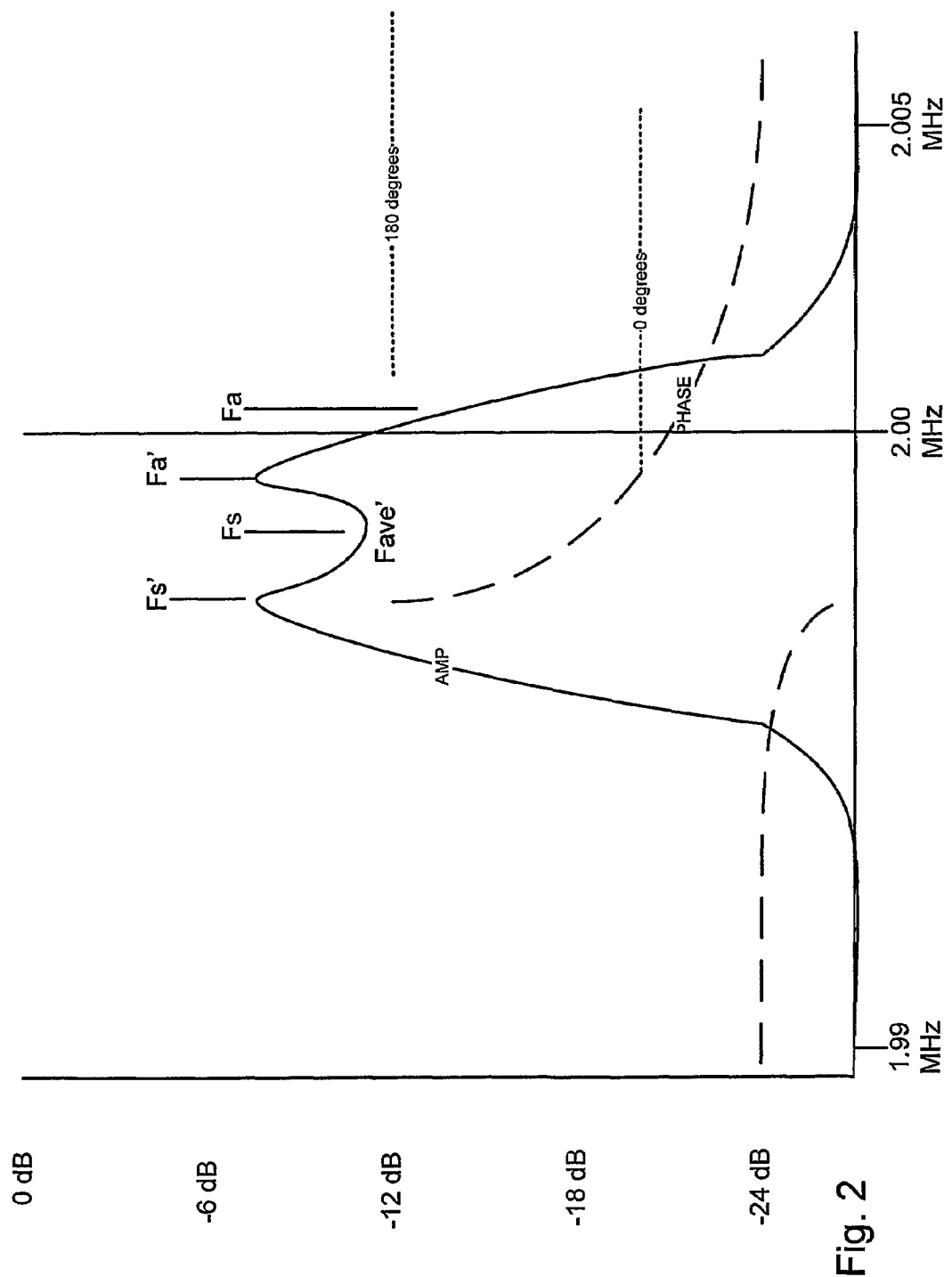
FIG. 2 is a graph depicting a typical frequency response of a simple two port, two pole device affected by mass loading due to added mass on at least one of its surfaces.
Figure 3:
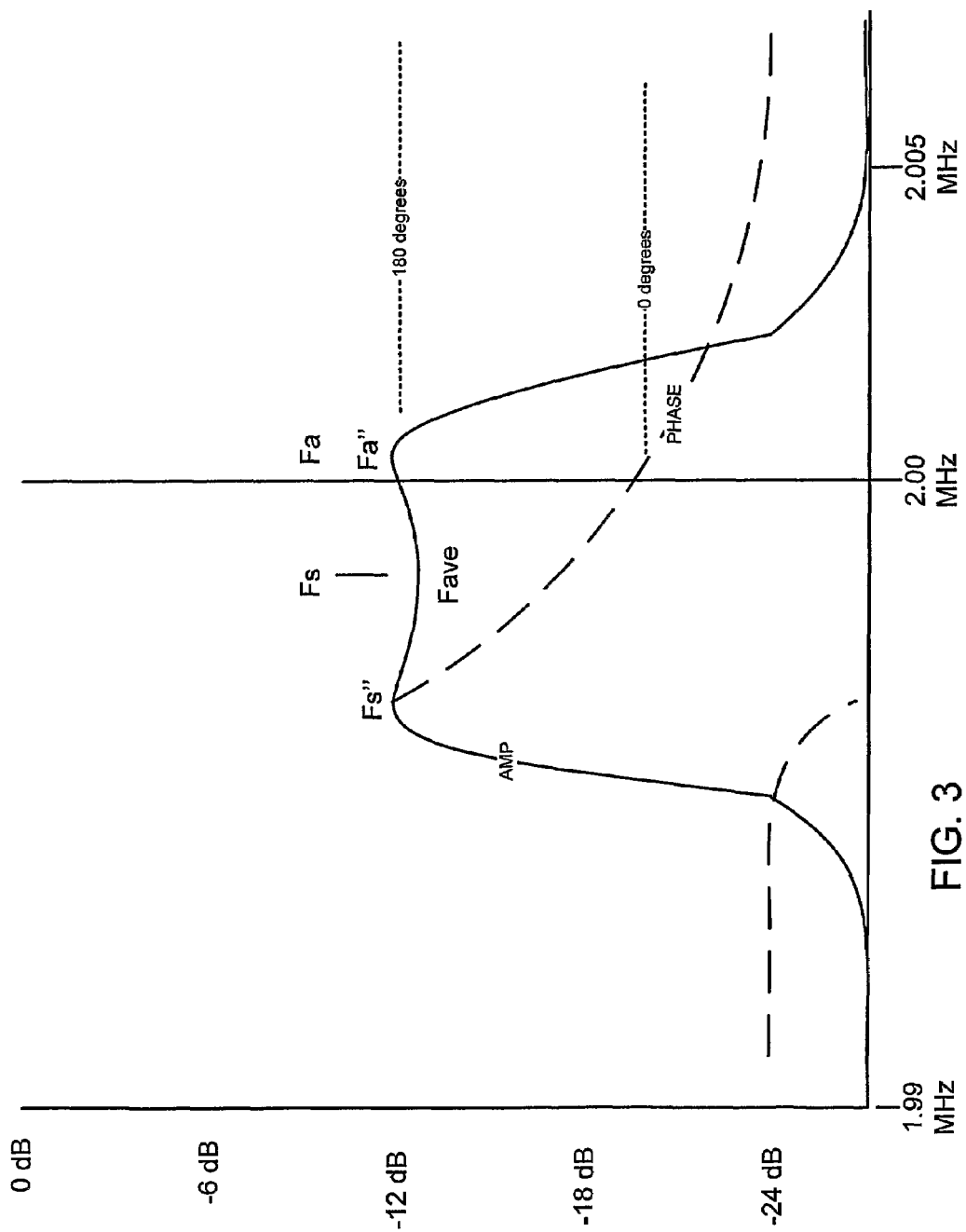
FIG. 3 is a graph depicting a typical frequency response of a simple two port, two pole device affected by damping due to the combined effects of viscous damping and density mass loading on at least one of its surfaces.

It has been experimentally observed that the two (or more) poles (i.e. resonant frequencies) move in unison, with essentially constant difference frequency, under lossless mass loading, as shown in FIG. 2; whereas the loss of power due to viscous damping alters the energy localization of the resonant cavities and thus also alters the frequency spread between the symmetric and antisymmetric frequencies, as well as the average frequency as shown in FIG. 3.

The invention employs an entrapment layer 420, preferably equally disposed over the first and second resonators and, more preferably, uniformly disposed over the entire sensing surface, to entrap a known volume of viscous liquid and enforce substantially rigid motion upon it via the textured surface of the entrapment layer. The effect of this rigidly entrapped liquid is to incur a corresponding downward frequency shift of the entire electrical response due to the mass loading phenomena, without altering the relative differences between the first and second resonant frequencies in the electrical response. The entrapment layer entraps a known volume of the measured fluid to the crystal, in a manner that will cause the fluid to behave as if it was rigidly attached to the crystal. Knowledge of the mass sensitivity coefficient of frequency, $S_m$, the entrained volume, V, the sensor area, A, and the downward frequency shift from an unloaded state, $\Delta F$, is sufficient to allow density to be estimated as $$\rho = \Delta F * A / V * S_m$$

The mass sensitivity coefficient may be estimated from perturbation theory using formulae that are specific to the given resonator structure and well known to one skilled in the art. This formula is directly analogous to the well known quartz crystal deposition monitor for solid films. This simplistic estimation ignores the role of viscosity as a source of error and assumes a suitable definition of the frequency of the electrical response. In the preferred embodiment of a two-pole, coupled resonator filter, the value of $\Delta F$ is the change of $F_A$, which has been experimentally observed to have minimal sensitivity to viscous loading, $S_V$.

Figure 4B:
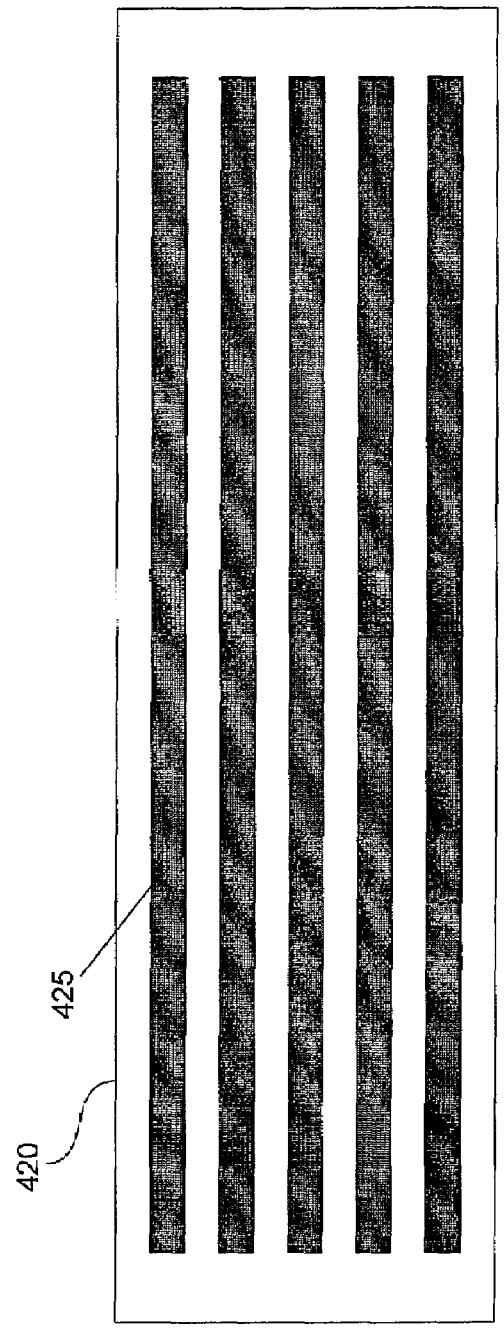

In the preferred embodiment the entrapment layer is implemented by providing grooves 425 in a metal film deposited on one surface of a piezoelectric crystal that is brought in contact with a fluid to be measured, as shown in FIG. 4. However other implementations of the entrapment layer may be provided, some of which are shown in FIG. 8. Thus for example the entrapment layer may be formed by pitting one or more surfaces of the crystal 800, or a coating layer thereon, in forms such as chambers 810, creating covered tunnels 820 (preferably open at both ends in the direction of flow), channels, and the like, either in the crystal 840 or by depositing material thereupon 830, or by a combination thereof. Most preferably, this is done by providing chambers or groves that are dimensioned to have a relatively small size in the direction of motion when compared to the wavelength of the sound wave induced in the fluid. A detailed discussion of options and considerations for texturing of the resonators is given in the Martin patents.

It should be noted that an entrapment layer need not necessarily be provided on the crystal face itself, but that an intermediate layer or layers may also be provided between the crystal and the fluid entrapment layer. Furthermore, the entrapment may occur by cutting, etching, drilling or depositing material, on the crystal face or on the intermediate layer.

As there are numerous methods of creating an entrapment layer, these specifications will relate to an entrapment layer as any layer being coupled to the acoustic wave device, or being integrated therein, having voids therein for entrapping a known volume of the measured fluid, in such a way that the entrapment layer causes a change in the resonant characteristics of the acoustic wave device due to the mass of the fluid trapped in the voids Prior experimental data in a smooth sensor, i.e. a sensor without an entrapment layer, shows that viscoelastic loading causes minimal (if any) frequency shift of the anti-symmetric resonance frequency, $F_A$, and substantial downward shift of the symmetric resonance frequency $F_S$. This indicates that $F_A$ is substantially compensated, by the inherent physics of the device, against viscosity variations. Data also has shown that simple mass loading, as would occur due to fluid entrapped in the entrapment layer, imparts equal frequency shifts to both resonant frequencies. While the nearly complete orthogonality between density and viscosity observed in the experimental data for $F_A$ may not occur for all designs, the effects of viscosity and density are mathematically separable in all cases and can be naturally separated by design in many cases.

Therefore, an aspect of the invention contemplates a densitometer using only the $F_A$ resonant frequency of a two-pole, coupled-resonator sensor having an entrapment layer. Such a densitometer would need to be calibrated for any residual dependence on viscosity in a given process to be highly accurate, but will provide a viable process monitoring method for relatively low precision applications merely using the natural orthogonality.

A densitometer as describe above would comprise an acoustic wave device with a coupled entrapment layer that is in contact with the measured fluid. As described above, the frequency characteristics change as a result of the trapped mass is represented as a frequency shift of both resonant frequencies $F_S$ and $F_A$.

Figure 5:
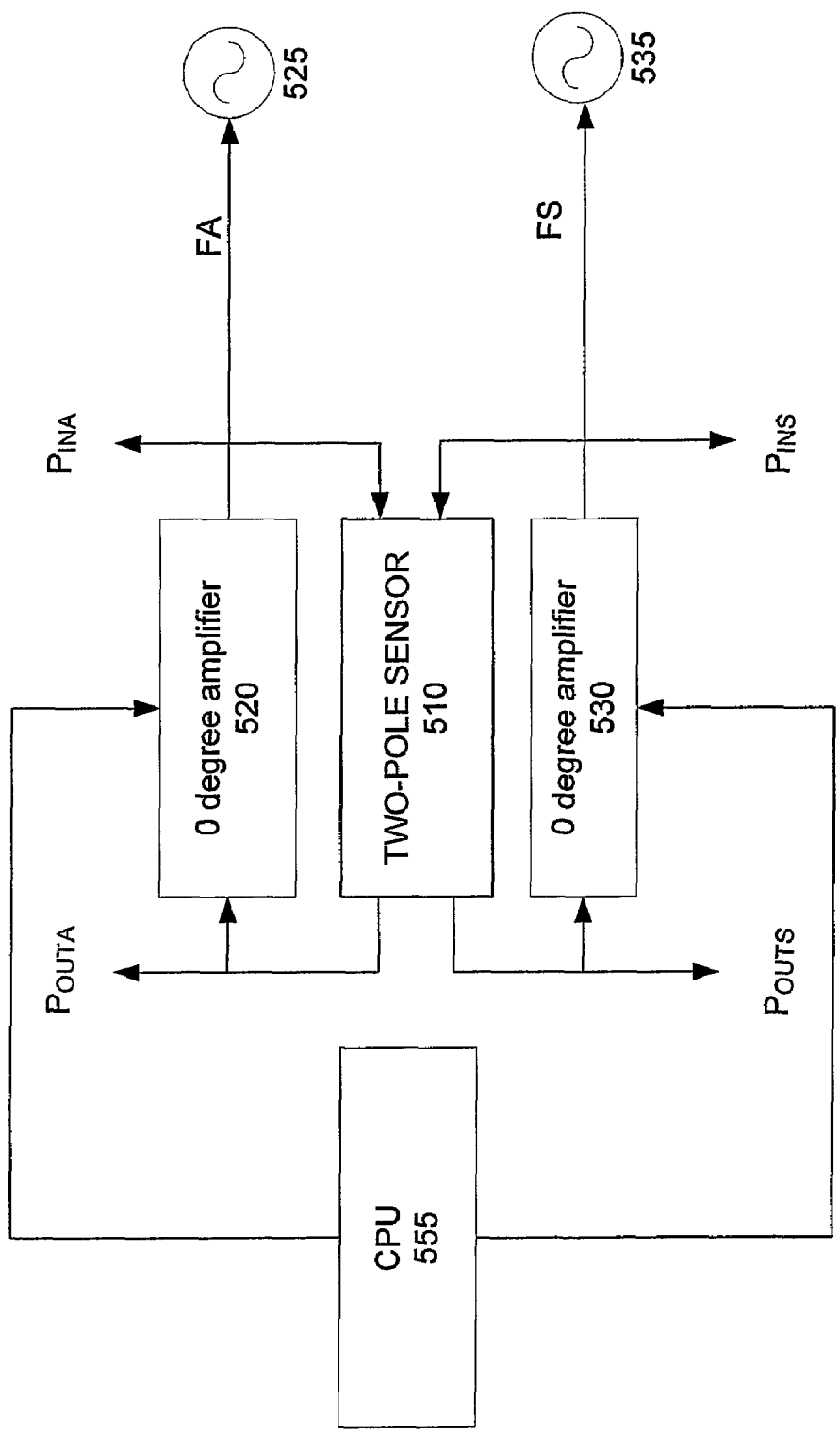
FIG. 5 is a simplified high level block diagram of a densitometer electronic circuitry.

The preferred simplest densitometer circuit contemplated in these specifications uses a subset of the block diagram of FIG. 5. The resonant frequency, $F_A$, is tracked by employing the sensor element, 510, as the feedback element of a zero-phase amplifier, 520. At the zero-phase resonance, $F_A$, oscillation will occur in this loop if the amplifier gain exceeds the sensor element loss and the net phase of the loop is substantially zero or a multiple of $2\pi$. The frequency is measured by frequency sensing apparatus such as a frequency counter, 525.

In order to measure the viscosity as well as the density, the resonant frequency $F_S$ is tracked by employing the sensor element 510 as the feedback element of a 180° amplifier 530, and a frequency sensing circuitry such as frequency counter 535. While not shown, the skilled in the art will realize that different circuitry is equivalently applicable for sensing the common mode frequency shift, such as frequency mixing, and the like. Using the methods of patent application Ser. No. 10/743,986 described above, the viscosity and shear rate may be measured using the sum and difference of power levels $P_{INA}$ and $P_{OUTA}$, or $P_{INS}$ and $P_{OUTS}$ respectively.

Figure 6:
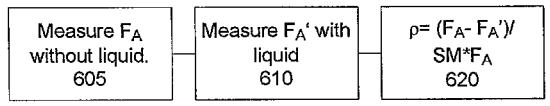
FIG. 6a represents a simplified data flow diagram for calculating density with an acoustic wave device having an entrapment layer.
FIG. 6b depicts a simplified flow diagram of frequency based density measurement and power loss viscosity measurement.
FIG. 6c depicts a simplified flow diagram for frequency based measurement of density and viscosity.
Figure 6:
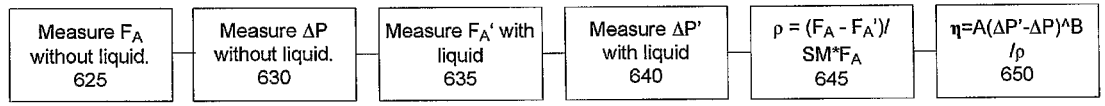
Figure 6:
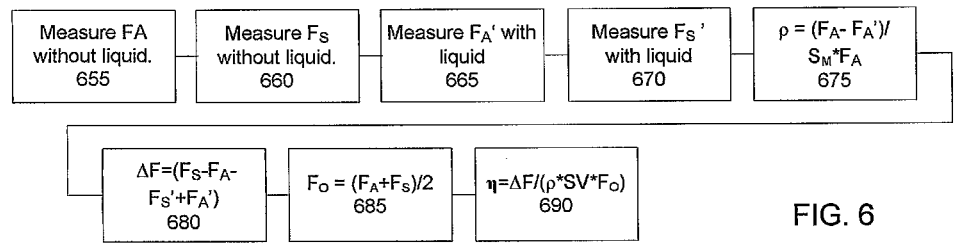

As seen in FIG. 6A, a simple method to measure density only involves measuring the resonant frequency, $F_A$, without any mass loading 605, applying the fluid to be measured to the sensor and measuring the resonant frequency, $F_A'$ being influenced by the mass of fluid entrapped in the entrapment layer 610. The frequency shift is calculated as the difference between the loaded $F_A'$ and unloaded $F_A$ resonant frequencies times a scale factor, $A*H(\eta)/S_M*V$, 620, where A is the effective area of the sensor, $H(\eta)$ is a calibration function to compensate for residual viscous effects, $S_M$ is the mass sensitivity of the LPAWD, and V is the volume of fluid entrapped in the entrapment layer. The first step of measuring $F_A$ without mass loading is not required for every measurement and may be done only once or as needed for calibration purposes.

It is also possible to measure the viscosity-density product of the liquid by measuring the power loss between the input and output transducers while simultaneously measuring the density via the frequency shift of the $F_A$ resonant frequency. Such a sensor could self-calibrate for the residual effects of viscosity on the density measurement and could provide data on acoustic viscosity ($\rho\eta$), intrinsic viscosity ($\eta$), or kinematic viscosity ($\eta/\rho$) as well as being a direct measurement of density.

If the orthogonality of viscosity and density effects on $F_A$ are insufficient, viscosity may be calculated, 650 using power level measurements, $P_{OUTA}$ and $P_{INA}$, or obtained from an external source. This data may then be used with predetermined calibration data to correct the density value. The corrected density is calculated as $\rho_{CORR} = A*H(\eta)*(F_A'-F_A)/(S_M*V)$, where $H(\eta)$ is a calibration function previously determined.

Data about the fluid viscosity 650 is estimated as above or obtained from an external source. The viscosity data is used to select an appropriate calibration table for the sensor acting at the assumed viscosity 650, and the table is used to compute the fluid density using the frequency shift obtained at step 635 and the appropriate table. Clearly, while all calculation steps may be made by hand, a computerized solution is preferable, and will be clear to those skilled in the art. Specialized circuitry that does not require specific software may also be utilized. It should also be noted that the viscosity effect may in some cases be minimal, and therefore the steps of selecting an appropriate calibration table may not be necessary. Naturally, the invention extends to such embodiment as well.

It is possible to simultaneously measure both the viscosity and the density by measuring both the symmetric and anti-symmetric resonant frequencies; wherein the difference between the frequencies is primarily dependent on viscosity-density product and the frequency of the second resonant frequency $F_A$ is primarily dependent on the density.

Note that while the density may be obtained by measurement of the antisymmetric frequency alone, the measurement is expected to provide better accuracy when compensated using viscosity information from the changes in $\Delta F = F_A - F_S$. Both resonant frequencies are measured in a reference medium, typically air, and in the liquid. The antisymmetric resonant frequency $F_A$ is measured as disclosed above. A second amplifier having 180 degree phase shift 530, is also connected between the input and output of the sensor element, 510. This second oscillator loop generates a signal with frequency, $F_S$, which is counted by frequency counter, 535. Switching elements control the two oscillators. Optionally the switching elements are replaced or complemented by other means of isolating the two feedback paths, such as cross-over networks. As connecting opposite phase amplifiers together may cause shorting of the amplifiers, cross talk problems, and the like, it is important to isolate the amplifiers. Many known examples exist, such as switching power to the amplifiers alternately, or switching the amplifier output as needed. In the preferred embodiment, CPU 555 controls the amplifiers' operation.

The change in the difference between the two frequencies between operation in air ($F_A - F_S$) and in the liquid, ($F_A' - F_S'$), is related to the product of density and viscosity while the change in $F_A$ is dependent on density. The nonlinear system of two equations in two unknowns is solved using standard numerical methods using a computer. While measuring $F_A$ is preferred by virtue of its minimal dependence on viscosity, any frequency point on the electrical response may be tracked and compensated for the viscosity-induced shifts of the measured frequency and that measuring phase changes at a constant frequency near the "measured frequency" is equivalent to measuring changes in that frequency.

Figure 7:
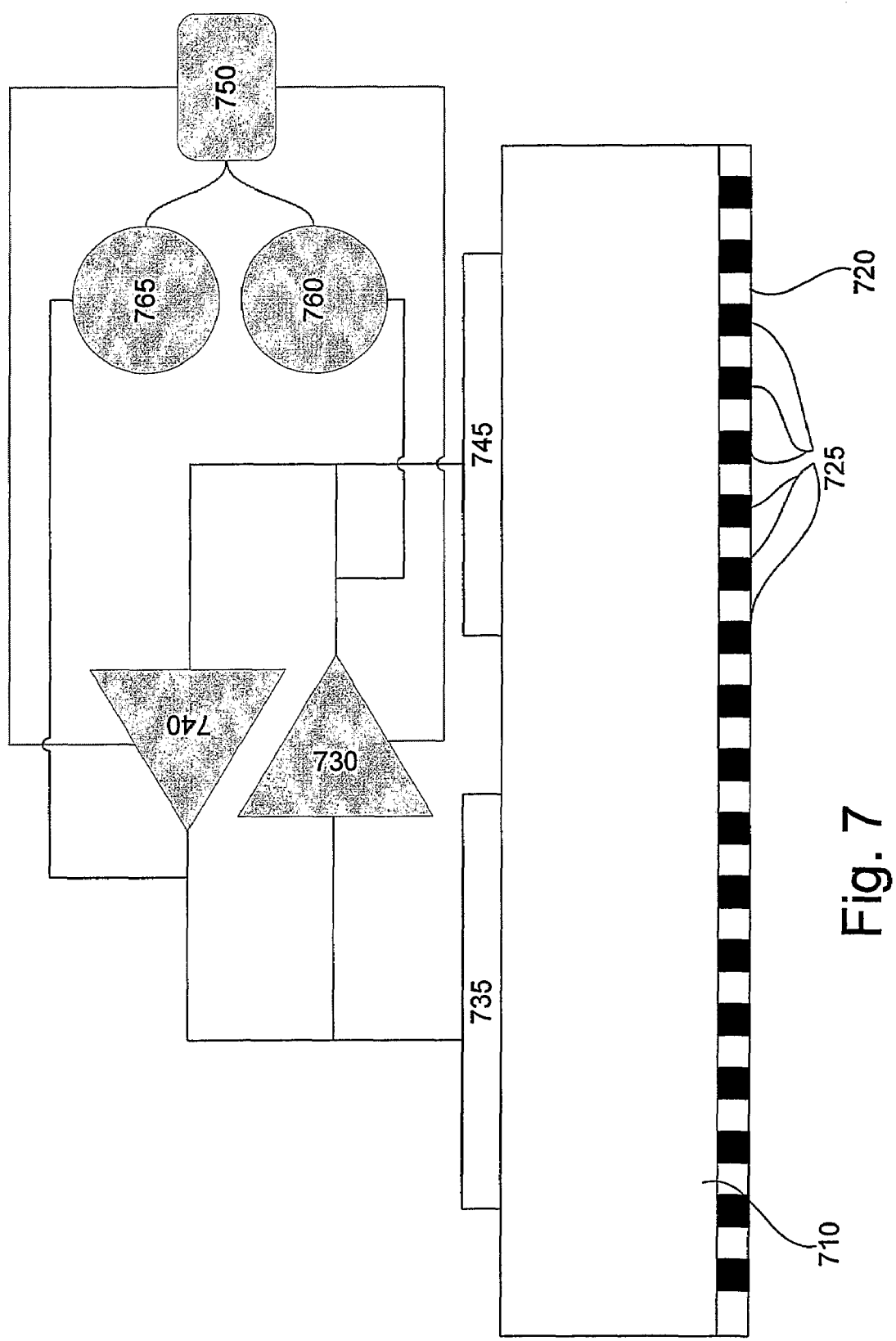
FIG. 7 depicts a simplified block diagram of circuitry for a density/viscosity sensor in accordance with the preferred embodiment.

FIG. 7 depicts a simplified circuitry block diagram of the preferred embodiment of the invention. An acoustic wave device 710 having an entrapment layer 720 formed as metalized layer with grooves 725 cut therein, covering substantially all of the acoustically active portion (that portion having acoustic energy trapped in resonant structures) of the face of the crystal in contact with the fluid. The grooves are relatively small in comparison with the wavelength of the acoustic wave in the fluid. Preferably, the grooved area covers all the area in contact with the fluid and the grooves occupy about 50% of the metalized area. The grooved area covers surface area of both of the coupled resonators and preferably an equal portion of each, most preferably covering all of the surface area of both resonators and the coupling region therebetween. Calculating the volume of the fluid trapped in the grooves is a matter of simple geometry, as the length, width and depth of the grooves are known.

Two amplifiers, a first having zero phase, 730, and a second having 180 degrees of phase shift of an electrical signal amplified therein, 740, are coupled between the input 735 and output 745 transducers. The amplifiers are connected through suitable switching circuits 750. At $F_S$, the LPAWD coupled resonator filter provides a transmission phase of typically 180° while at anti-symmetric frequency $F_A$ it provides typically 0° transmission phase shift. Amplifier 740 will oscillate on $F_s$ and amplifier 730 will oscillate on. $F_A$. Supporting coupling/decoupling, gain setting, and other common components needed for the operation of the amplifiers as oscillators are well known and not discussed herein. While frequency counters, 760 and 765, are proposed, alternate means including frequency to voltage converters or the use of mixers to obtain difference frequencies and sum frequencies are equally applicable and contemplated herein, but as those are well known techniques, are not detailed or shown.

In these specifications, elasticity and viscosity are the real and imaginary parts of the complex viscoelastic modulus, $\mu + j\omega\eta$. It is widely desired in materials analysis to characterize the viscoelastic properties as a function of shear rate and temperature without errors due to inadequate knowledge of the associated density.

It should be noted that non-Newtonian liquids would yield differing viscosity estimates based on frequency data and on power loss data. The viscoelastic effect is unequal on these terms in a non-Newtonian (e.g. Maxwellian) fluid. The inventor therefore further contemplates measuring density, viscosity, effective shear elasticity, and shear rate simultaneously by employing both $\Delta F$ and power loss data to obtain both the real (elasticity) and imaginary (viscosity) components of viscoelasticity while using $F_{AVE}$ and average power to obtain the density and shear rate data. Using the methods of U.S. patent application Ser. No. 10/743,986 described above, it is possible further to perform this calculation over a range of shear rates. Since density is independent of shear rate, it is possible to eliminate errors in the separation of density and viscoelasticity that may occur due to measurement errors associated with non-Newtonian viscosity. Such schemes and algorithms would be considered equivalent by one skilled in the art.

Therefore in the most preferred embodiment of the invention is a device and methods for the independent measurement of density, the simultaneous measurement of density and viscosity, and/or the simultaneous measurements of density and complex viscoelasticity of a sample at a known shear rate. The device utilizes a coupled-resonator filter in contact with the sampled liquid via an entrapment layer. The resonator filter has two or more mutually coupled resonant cavities, at least one of which is coupled to an input transducer and at least one of which is coupled to an output transducer, and therefore provides at least a two pole electrical transfer function from the input terminal to the output terminal. The device may be succinctly described as a two-port (separate inputs and outputs), multi-pole (multiple separate resonant frequencies), textured-surfaced, coupled-resonator filter. The method for using the device involves coupling the entrapment layer to the fluid to be measured, exciting the device by an alternating electrical energy provided to the input transducer. Measuring the power insertion loss, i.e. the difference between the power inputted to the input transducer and the power at the output of the output transducer, provides a measure of the intrinsic viscosity of the fluid times its density ($\eta\rho$). Controlling the input power level provides a mechanism for controlling the shear rate at which the viscosity measurement is preformed. Measuring the frequency shift by measuring a first resonant frequency $F_S$ and a second resonant frequency $F_A$ as described above. The frequency shift of $F_A$ is primarily attributed to the mass loading due to the entrapped fluid, while the frequency shift and/or amplitude change of both resonant frequencies $F_S$ and $F_A$ provide data from which the viscosity-density product is derived. As the viscosity is known from either the insertion loss or difference frequency measurement steps above, and the volume of the fluid trapped in the entrapment layer is known from the entrapment layer geometry, deriving the density of the fluid from the data is a matter of mathematical manipulation well known in the art. Most preferably an independent temperature measurement is also taken to relate the measured/calculated parameters to specific temperature.

The fields in which the invention may be practiced are widely varied. By way of a non limiting example, the invention may be used to measure viscosity and density in situ within a manufacturing process such as quality of slurry in paper making or casting operations, ink in printing processes, plastic material in casting or injection operations, biological and chemical medical processing, distillation processes such as oil refinery, and the like. The invention may similarly be used to monitor fluid characteristics of operational fluids such as oil and fuel in engines, turbines and other machinery, during machine operation or by sampling. Furthermore, the invention may be used in material analysis utilizing small samples, to aid in identifying the material composition. Clearly the invention will be beneficial for analyzing liquid, semi-liquid, and in some cases gaseous end products such as milk, oil, acetylene and other heavy gasses, pre-made slurry, concrete, fuel oils, and the like. Other uses will be clear to those skilled in their respective arts in which a compact, robust and accurate measurement of density and viscosity are of value.

It will be clear to those skilled in the art that the physical structures, the calculations, process flow, and other details provided above are but examples of how to make and/or use the various aspects of the invention, and that one skilled in the art would be able to provide numerous changes to the order of steps, the structure, software, and the electronic circuitry described above, given the flexible nature of electronics and software. While there has been provided a complete description of what is at present believed to be the best methods to practice the invention, the invention is clearly directed at covering such modifications and equivalents as will be clear to those skilled persons, and not limited to the logical block arrangement, algorithms, electronic circuitry, physical aspects, or other aspects of the description and drawings provided by way of non-limiting example only.

The invention claimed is:

1. A method for measuring fluid density comprising the steps of:
   Providing a sensor comprising a liquid phase acoustic wave device (LPAWD) having an entrapment layer coupled thereto, the entrapment layer having a textured surface in contact with said fluid, and having a known volume available for entrapping said fluid; the LPAWD comprising an input and an output transducers electromechanically coupled respectively to a first and second resonators, said first and second resonators being sufficiently coupled therebetween to provide said LPAWD with an electrical transfer function characterized by at least a first resonant frequency $F_S$ and a second resonant frequency $F_A$ at or about 180 phase shift relative to said $F_S$;
   feeding an input electrical signal to said input transducer;
   using said sensor measuring the density of the fluid.

2. A method for measuring fluid density according to claim 1 wherein said step of measuring further comprises the steps of:
   measuring said second resonant frequency; and,
   using said measured resonant frequency, and characteristic response of said LPAWD, calculating the density of the fluid.

3. A method for measuring fluid density according to claim 1, wherein said textured surface covers an approximately equal area of each of said resonators.

4. A method for measuring fluid density according to claim 1 wherein said step of measuring further comprises the step of using a calibration function to account for an approximated viscosity of said fluid.

5. A method for measuring fluid density according to claim 1 further comprising the steps of:
   providing an amplifier coupled between said input and output transducers, said amplifier having a gain sufficiently high to cause signals therethrough to oscillate at or about said second resonant frequency $F_A$; and,
   providing a frequency sensing circuit to sense changes in the frequency of oscillations.

6. A method of measuring density and viscosity of a fluid the method comprising the steps of:
   providing a sensor comprising a liquid phase acoustic wave device (LPAWD) having an entrapment layer coupled thereto or embedded therein, the entrapment layer having at least one textured surface for contact with said fluid, and having a known volume available for entrapping said fluid; the LPAWD comprising an input and an output transducers electromechanically coupled respectively to a first and second resonators, said first and second resonators being sufficiently coupled therebetween to provide said LPAWD with an electrical transfer function characterized by at least a first resonant frequency $F_S$, and a second resonant frequency $F_A$ at or about 180 phase shift relative to said $F_S$;
   feeding an input electrical signal to said input transducer;
   using said sensor measuring the density of the fluid; and,
   measuring the viscosity of the fluid.

7. A method of measuring density and viscosity according to claim 6, wherein said input electrical signal is controlled to produce a predetermined shear rate under which said viscosity is being measured.

8. A method of measuring density and viscosity according to claim 7, wherein said shear rate is controlled by controlling said input electrical signal at an energy level, $P_{IN}$, to produce a desired displacement of said entrapment layer.

9. A method of measuring density and viscosity according to claim 8, wherein said energy level, $P_{IN}$, is calculated so as to obtain the requisite amplitude, U, to provide the desired shear rate, $\dot{\gamma}$, using the formulae: $U=\delta\dot{\gamma}/\omega$, where $\omega=2\pi F_A$ is the radian frequency $$\delta = \sqrt{\frac{2\eta}{\omega\rho}}$$

is the penetration depth of the wave into a fluid having viscosity, $\eta$, and density, $\rho$, and the acoustic wave amplitude $U=C\sqrt{P_{avg}}$ determined by a device constant, C, and an energy level, $P_{avg}$, being a geometric mean of power levels measured at said input $P_{IN}$ and output $P_{out}$ transducers.

10. A method of measuring density and viscosity according to claim 6 further comprising the step of measuring the power difference between the input and output transducers, to obtain a product of the viscosity and density of said fluid.

11. A method of measuring density and viscosity according to claim 6, wherein said step of measuring the density comprises measuring said second resonant frequency, $F_A$.

12. A method of measuring density and viscosity according to claim 6, wherein said textured surface covers an approximately equal area of each of said resonators.

13. A method of measuring density and viscosity according to claim 6, wherein said step of measuring the viscosity comprises measuring a product of viscosity and density, and further comprises the step of utilizing the measured density and said product.

14. A method of measuring density and viscosity according to claim 6, further comprising the step of using the measured viscosity to compensate for viscosity effects in said step of measuring density.

15. A method of measuring density and viscosity according to claim 6, wherein said step of measuring the density comprises measuring the said second resonant frequency, and wherein said step of measuring the viscosity comprises measuring power insertion loss between said input resonator and output resonator.

16. A method of measuring density and viscosity according to claim 6, wherein said step of measuring the viscosity comprises measuring the shift of one or both of said resonant frequencies.

17. A method of measuring density and viscosity according to claim 6, further comprising the step of controlling the energy level of said input electrical signal so as to control the shear rate in which said viscosity is measured;

wherein said step of measuring density comprises measuring the frequency shift of said second resonant frequencies; and, wherein said step of measuring the viscosity comprises measuring the power insertion loss between said first and second resonator.

* * * * *